United States Patent [19]

Sessions et al.

[11] Patent Number: 5,254,301
[45] Date of Patent: Oct. 19, 1993

[54] PROCESS FOR PREPARING A SHEET OF POLYMER-BASED FOAM

[75] Inventors: Robert W. Sessions, Hinsdale; Roy D. Carr, Burr Ridge; Peter E. Morin, Orland Park, all of Ill.

[73] Assignee: Ferris Mfg. Corp., Burr Ridge, Ill.

[21] Appl. No.: 14,044

[22] Filed: Feb. 5, 1993

Related U.S. Application Data

[63] Continuation of Ser. No. 422,954, Oct. 18, 1989, abandoned, which is a continuation-in-part of Ser. No. 175,036, Mar. 29, 1988, Pat. No. 5,064,653.

[51] Int. Cl.⁵ ............................................. B29C 67/22
[52] U.S. Cl. ............................. 264/46.2; 264/46.3; 264/46.4; 264/55
[58] Field of Search ............... 264/46.2, 46.3, 45.1, 264/46.4, 321, 55; 156/79

[56] References Cited

U.S. PATENT DOCUMENTS

| | | | |
|---|---|---|---|
| 734,423 | 7/1903 | Liepmann | 156/78 |
| 2,720,477 | 10/1955 | Lancaster | 128/156 |
| 3,062,210 | 11/1962 | Scholl | 128/156 |
| 3,193,406 | 7/1965 | Mittelman | 156/79 |
| 3,298,884 | 1/1967 | Willy | 156/79 |
| 3,328,225 | 6/1967 | Urbanic et al. | 161/89 |
| 3,331,728 | 7/1967 | Lane | 128/156 |
| 3,399,671 | 9/1968 | Satas | 128/156 |
| 3,444,859 | 5/1969 | Kalwaites | 128/284 |
| 3,655,918 | 5/1972 | Lindquist et al. | 128/156 |
| 3,709,752 | 1/1973 | Wistozky et al. | 156/79 |
| 3,748,217 | 7/1973 | May et al. | 156/78 |
| 3,903,232 | 9/1975 | Wood et al. | 264/157 |
| 3,959,049 | 5/1976 | Tanaka et al. | 156/79 |
| 3,965,229 | 6/1976 | Driscoll | 156/79 |
| 3,977,406 | 8/1976 | Roth | 264/321 |
| 3,984,195 | 10/1976 | del Carpio | 264/46.2 |
| 4,137,360 | 1/1979 | Reischl | 264/41 |
| 4,279,964 | 7/1981 | Heller | 427/365 |
| 4,347,281 | 8/1982 | Futcher et al. | 264/46.2 |
| 4,360,015 | 11/1982 | Mayer | 128/156 |
| 4,362,585 | 12/1982 | de Antonis et al. | 156/62.2 |
| 4,414,970 | 11/1983 | Berry | 128/156 |
| 4,524,064 | 6/1985 | Nambu | 424/81 |
| 4,562,110 | 12/1985 | Tong | 128/156 |
| 4,569,861 | 2/1986 | Smith et al. | 427/387 |
| 4,603,076 | 7/1986 | Bowditch et al. | 428/316.6 |
| 4,622,089 | 11/1986 | Lauritzen | 128/156 |
| 4,660,553 | 4/1987 | Naylor et al. | 128/156 |
| 4,661,099 | 4/1987 | Von Bittera et al. | 128/156 |
| 4,764,420 | 8/1988 | Gluck et al. | 264/46.2 |
| 4,773,409 | 9/1988 | Cilento et al. | 128/156 |
| 4,938,819 | 7/1990 | Ishii et al. | 264/46.2 |

Primary Examiner—Allan R. Kuhns
Attorney, Agent, or Firm—Leydig, Voit & Mayer

[57] ABSTRACT

A continuous process for the preparation of a polymer-based foam sheet at ambient temperatures wherein the foam is produced from a reaction product capable of curing at ambient temperatures formed by the reaction of a reactant composition comprising a prepolymer, such as an isocyanate-capped polyether, and water, comprising:

(a) providing a continuous substrate;
(b) depositing said reaction product onto said substrate;
(c) compressing said reaction subjecting said product to at least one compression of a predetermined degree after said reaction product has creamed but prior to the time said reaction product has finally cured; and
(d) finally curing said reaction product.

61 Claims, 1 Drawing Sheet

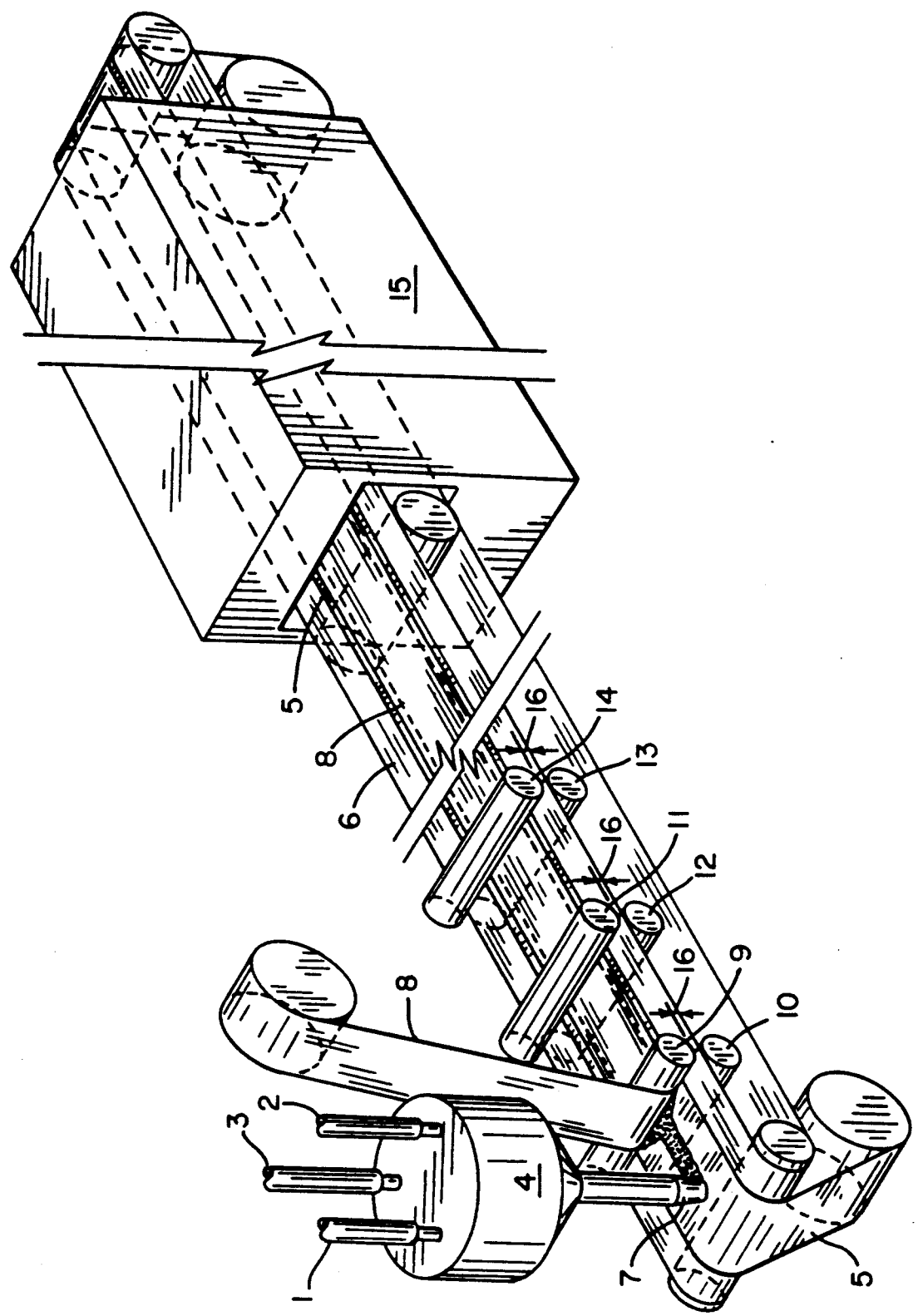

PROCESS FOR PREPARING A SHEET OF POLYMER-BASED FOAM

RELATED APPLICATIONS

This is a continuation of copending application Ser. No. 07/422,954 filed Oct. 18, 1989, now abandoned, which is a continuation-in-part of U.S. patent application Ser. No. 175,036, filed Mar. 29, 1988, by Robert W. Sessions and Roy D. Carr entitled "Hydrophilic Foam Compositions."

BACKGROUND OF THE INVENTION

1. Field of the Invention

The present invention relates to a novel process and apparatus for the production of foam products and, more particularly, a process and apparatus for preparing a polymer-based foam of a predetermined thickness that is produced without the need to slice a larger foam bun to the desired thickness. The resulting foam is suitable for use optimally as a surgical or medical dressing.

2. Background of the Invention

Historically, the treatment of wounds involved the application of sterile dressings such as gauze and lint to the injured area, both with and without the use of an antiseptic or curative substance. These dressing materials, however, suffer from a disadvantage in that they adhere to the surface being treated or leave fibers in the wound thereby prolonging the recovery period. In an attempt to circumvent the difficulties associated with the use of these materials, recent research and development efforts have yielded new products which are centered around the use of synthetic materials as wound dressings.

The processes by which these synthetic materials, such as films and sponges, are manufactured, vary according to the composition of the synthetic material and the properties desired in the final product. Nevertheless these processes possess many similarities. Generally, each process involves formulating a polymer-based foam precursor, providing a substrate, applying this foam precursor onto the substrate, and curing the resulting foam by applying heat. Such processes are typically extended by slicing a relatively thick foam bun into a final product having the desired thickness. However, the combination of the use of heat to effect curing as well as slicing the resulting product to the desired thickness increase the cost of the final product. Moreover, in the latter case, the addition of an extra step during production significantly lowers the overall efficiency of the process.

The determination of the amount of heat to effect curing of the foam material is further complicated by the desire to retain a certain amount of moisture in the final foam product. This moisture is preferred as it acts to enhance the appearance, texture, and wettability of the product. Thus, the use of heat to effect curing necessitates a complex analysis to determine the optimal amount of heat to use during the curing phase which will effect the proper curing of the foam while not resulting in the final product having less than the desired degree of moisture. Therefore, it would be advantageous to provide a process which would enable a manufacturer to easily produce a polymer-based foam product having a predetermined degree of moisture without necessitating the performance of a complex curing versus moisture loss analysis.

U.S. Pat. No. 4,660,553 illustrates a method for making a medical dressing. This process comprises applying a layer of a foamable silicone elastomer onto a substrate which is an absorbent for the composition. A scraper blade or the like is then used to distribute a critical amount of the elastomer onto the substrate. Reinforcing material is subsequently placed into the elastomeric composition and the reinforced foam is allowed to finally cure. In order to effect curing, the foam may be subjected either to ambient temperatures or to heat, the heat being applied to hasten or increase the degree of cure. After the foam has finally cured, the substrate is cut away from the foam product to produce a flexible, reinforced elastomeric foam sheet. The manner in which the elastomer is applied onto the substrate is the only means by which the thickness of the final foam product may be controlled in this process.

U.S. Pat. No. 3,959,049 discloses a process for making air permeable artificial leathers. This process comprises incorporating a catalyst, foam stabilizer, and optionally a pigment, into an isocyanate-terminated polyurethane prepolymer thereby forming a solvent free "paint". After the "paint" is formed, it is coated onto release paper and a substrate is applied over the exposed portion of the "paint". Subsequently, the foaming and polymerization reactions proceed in an atmosphere having a dry-bulb temperature between 40° C. to 95° C. and a relative humidity of at least 60 percent. The presence of heat and water at this stage of the process causes the reaction to advance. During the course of this reaction, the assemblage is passed through rollers which compress the assemblage. After the compression is completed, Examples 1-4 show the assemblage being placed in a dryer at 130° C. for three minutes to further advance the foaming and polymerization reactions. The release paper is removed subsequent to this drying procedure.

Despite the variety of methods for the production of synthetic foams, there remains a need for a process for manufacturing a foam in which the thickness of the resulting foam may be accurately controlled. Further, this thickness should optimally be attainable without requiring a final slicing procedure. Moreover, it would also be advantageous if the process were more energy efficient, with no heating of the foam being required to effect the curing of the foam product.

Accordingly, it is a principal object of the present invention to provide a method for the continuous production of a polymer-based foam in which the thickness of the resulting product may be very accurately controlled.

A related object is to provide a method for the continuous production of a polymer-based foam in which the foam is formed directly to a predetermined thickness without the need to slice the foam to the desired thickness after curing.

Yet another object is to achieve a final product having a predetermined moisture level.

It is a further object of the present invention to provide a process for preparing a polymer-based foam product which is more efficient than prior processes wherein the application of heat to effect the curing of the product is not required.

An additional object is to provide an apparatus for accomplishing the aforesaid objects.

These and other objects and advantages of the present invention will be apparent from the following description of the invention.

SUMMARY OF THE INVENTION

The present invention is predicated on the discovery that a sheet of polymer-based foam of predetermined thickness may be produced directly, and without the need for slicing the finally cured foam. In accordance with the present invention a foam of predetermined thickness may be made from the reaction product of a reactant composition capable of curing at ambient temperatures which comprises (a) a prepolymer and (b) water, by providing a continuous substrate, depositing the reaction product onto the substrate, covering the reaction product with a cover sheet to form a composite, compressing the composite to a predetermined degree after the reaction product has creamed, but prior to final curing thereof to produce a foam having the desired thickness, and finally curing the foam. After the reaction product is deposited onto the substrate and until such time as the foam is finally cured, the process is conducted at ambient, or room, temperature.

In a further embodiment of the invention, there is provided an apparatus suitable for the continuous preparation of a sheet of polymer-based foam of a predetermined thickness that may be produced directly, and without the need for slicing the finally cured foam, from a reaction product comprising a reactant composition capable of curing at ambient temperatures comprising a prepolymer and water. The apparatus comprises means for reacting said reaction composition, means for providing a continuous substrate, means for depositing said reaction product onto said substrate, means for covering said reaction product with a cover sheet to form a composite, and means for compressing said composite to a predetermined degree after said reaction product has creamed but prior to the final curing thereof to produce a foam having the desired thickness. After the reaction product is deposited onto said substrate, said foam is processed at ambient temperature until said foam is finally cured.

While the invention will be described in connection with the preferred embodiment, it is understood that the invention is not intended to be so limited. On the contrary, it is intended to cover all alternatives, modifications, and equivalents as may be included within the spirit and scope of the invention as defined by the appended claims. As an example, while the present invention will be described herein as primarily useful for the production of surgical and medical dressings, it should be appreciated that the method is useful for the production of other polymer-based foam products as well.

BRIEF DESCRIPTION OF THE DRAWING

The FIGURE is a schematic diagram of an apparatus used to form the foam sheet.

DETAILED DESCRIPTION OF THE PREFERRED EMBODIMENT

The present invention comprises a method and apparatus for the production of a foam sheet having a predetermined thickness. Further, it is contemplated that this sheet may be produced by curing the foam not at elevated temperatures, but at ambient temperature.

In view of the foregoing objects and requirements, it is therefore desirable to select a foam prepolymer that is capable of curing at ambient temperature. Moreover, the prepolymers chosen should also be capable of foaming in an aqueous system in the absence of a catalyst; however, they should not dissolve in the aqueous liquid. Additionally, it is highly desirable that these prepolymers cure to form a porous cellular foam matrix, this matrix enabling both the absorption of external fluids and carriage of the chosen adjuvant by the resulting foam composition. The formation of this cellular foam matrix is preferred due to the large volume that is available not only for absorption, but also to contain the chosen adjuvant.

Prepolymers contemplated by the present invention are preferably used for the production of a medical or surgical dressing, thus they must also be safe for use in the human body. Generally, polyurethane prepolymers are suitable, and optimally, an isocyanate-capped prepolymer is used.

Isocyanate-capped polyether prepolymers, such as those disclosed in U.S. Pat. Nos. 3,903,23 and 4,137,200, are suitable for use in the present invention. Such prepolymers should preferably have a defined average isocyanate functionality greater than 2. These prepolymers may be capped with aromatic isocyanates, such as, for example, toluene diisocyanate or methylene diphenyl isocyanate, or with aliphatic isocyanates, such as isophorone diisocyanate. Specific isocyanate-capped polyether prepolymers which have been found suitable for use in the practice of the present invention include prepolymers sold under the trademark HYPOL (W. R. Grace & Co., Lexington, Mass.). Examples include HYPOL FHP 2000, HYPOL FHP 2002, HYPOL FHP 3000, HYPOL FHP 4000, HYPOL FHP 5000, HYPOL X6100, and HYPOL hydrogel.

HYPOL 2000, HYPOL 2002, and HYPOL 3000 prepolymers are derived from toluene diisocyanate. FHP 2000 and FHP 2002 both have an equivalent weight (per NCO) of 625, an NCO content of 1.60 meq/g and a specific gravity of 1.19. The viscosity of FHP 2000 is 18,500 cps (Brookfield LVF, #4 Spindle, 12 rpm at 25° C.) and that of FHP 2002 is 20,000. FHP 3000 has an equivalent weight (per NCO) of 425, an NCO content of 2.35 meq/g, a specific gravity of 1.15 and a viscosity (measured as described above) of 10,500. HYPOL hydrogel is likewise derived from toluene diisocyanate. It has an NCO content of 0.5–0.9 meq/g and a viscosity of 10,000 to 12,000 cps at 25° C.

Another example of an isocyanate-capped prepolymer suitable for use in the present invention is AQUAPOL prepolymer, commercially available from Freeman Chemical Corporation. AQUAPOL prepolymers, which are derived from toluene diisocyanate, have an NCO-value of 2.5 to 3.0 and are formed from the reaction of toluene diisocyanate and an organic polyether polyol containing at least 40 percent by weight ethylene oxide adducts as described at Col. 2, lines 3–22 of U.S. Pat. No. 4,517,326.

A further example of an isocyanate-capped prepolymer suitable for use in the present invention and which is derived from toluene diisocyanate is sold under the trademark TREPOL. This prepolymer is commercially available from Twin Rivers Engineering. TREPOL prepolymers have an NCO content of 1.4 meq/g and a viscosity at 90° C. of 4,700 cps.

The HYPOL FHP 4000 and HYPOL FHP 5000 prepolymers are derived from methylene diphenyl diisocyanate. FHP 4000 has an equivalent weight (per NCO) of 476, an NCO content of 2.10 meq/g, a Brookfield viscosity (LVF, #4 Spindle, 12 r.p.m. at 25° C.) of 20,000 and specific gravity of 1.17. FHP 5000 has an equivalent weight (per NCO) of 392, an NCO content of 2.55 meq/g, a Brookfield viscosity (measured as for FHP 4000) of 18,000 and a specific gravity of 1.17.

Another example of an isocyanate-capped prepolymer suitable is HYPOL X6100. This prepolymer is derived from isophorone diisocyanate and has an NCO content of 1.8 meq/g and a viscosity at 25° C. of 12,000 cps.

The amount of prepolymer in the reactant composition used to prepare the hydrophilic foam composition is not particularly critical, but depends on a number of factors as will be described in greater detail hereinafter. One factor is the proportion of other components in the reactant composition. However, there should be sufficient prepolymer to form a polyurethane foam, to releasably contain an adjuvant, if desired, and to adequately contain hydrophilic agent. To that end, the ratio of prepolymer to hydrophilic agent should be such that the reactant composition does not degrade or break-up into its separate constituents. Furthermore, while there should be sufficient prepolymer to provide integrity to the foam, there should not be so much prepolymer that the resulting polyurethane composition becomes unworkable. Where the final composition is to be applied to the skin, the resulting foam composition is desirably relatively smooth and soft while exhibiting the desired absorbance characteristics so that it does not irritate or otherwise harm the skin.

The concentration of prepolymer further depends on its isocyanate functionality and the degree of crosslinking desired in the final foam product. In general, the greater the isocyanate functionality, the greater the degree of cross-linking in the cured foam product. Typically, the reactant composition will comprise from about 20% to about 60% by weight prepolymer. Preferably the reactant composition will comprise from about 45% to about 50% by weight of the prepolymer. Advantageously, the prepolymers may be used alone or in combination.

The reactant composition may, if desired, further include a hydrophilic agent which is incorporated into the foam composition to absorb external liquid, such as wound exudate, and to retain such liquid in the composition. When applied to a wound, the hydrophilic agent is believed to work in conjunction with the foam to hold moisture at the surface of the wound. This allows healing agents exuded by the foam to be concentrated and held at the wound surface. At the same time, the hydrophilic agent incorporated into the foam composition is believed to absorb fluid from the wound to assist thickening of the blood, i.e., it serves as a hemostat. Absorption of exudate by the hydrophilic agent, and the subsequent swelling of the agent results in the removal of inflammatory exudates and particles that would otherwise hinder tissue repair or cause eschar formation. Necrotic debris and bacteria are likewise removed as autolysis, i.e. chemical debridement, is stimulated.

The hydrophilic agent is preferably a highly absorbent polymer, commonly known as a superabsorbent polymer. One measure of polymer absorbency is its fluid uptake capability, well known by those skilled in the art. Hydrophilic agents suitable for use in the present invention include polymers that are capable of absorbing at least fifty times their weight of water, that is, such agents have a fluid uptake of at least 50 ml/g. Hydrophilic agents having an even higher fluid uptake, such as of at least about 100 ml/g and even higher are also acceptable, with those having an uptake of at least about 150 ml/g being preferred. Suitable superabsorbent polymers include sodium and aluminum salts of starch, grafted copolymers of acrylates and acrylamides, and combinations thereof, as well as polyacrylate salts. Of course, other absorbent materials may be used in combination with such highly absorbent polymers, provided the fluid uptake of the overall combination used for the hydrophilic agent is greater than 50 ml/g. When such agents are employed, either alone or in combination, the resulting foam composition desirably has the ability to hold at least about three times its weight in liquid. In the preferred embodiment, the resulting foam composition will have the ability to tightly hold at least about three times its weight in fluid. As used herein "tightly held" or "tightly bound" liquid means the relative amount of liquid retained by the sample after compression. More specifically, retained liquid is the unit weight of liquid per unit weight of foam. It is determined by the formula:

$$\text{Retained Liquid} = \frac{(\text{Wt. of Foam Sample Plus Absorbed Liquid}) - (\text{Weight of Foam Sample})}{\text{Weight of Foam Sample}}$$

Tightly held liquid is a measure of the relative amount of liquid retained by the sample after compression. It is determined by rolling an 8 pound roller over the sample ten times, and then, using the retained liquid formula to calculate the relative proportion of liquid that was not squeezed out of the composition.

Hydrophilic polymers which have been found suitable for use in the foam composition of this invention are commercially available from Grain Processing Corporation. These polymers include a starch-g-poly(2-propenamide-co-2-propenoic acid, mixed sodium and aluminum salt) sold under the trademark WATER LOCK A-222; a starch-graft copolymer of polyacrylic acid and polyacrylamide having the chemical name starch-g-poly(2-propenamide-co-2-propenoic acid, sodium salt), sold under the trademark WATER LOCK A-100; a starch g-poly(2-propenamide-co-2-propenoic acid, sodium salt), sold under the trademark WATER LOCK A-200. Superabsorbent polymers commercially available from Grain Processing Corporation under the trademark WATER LOCK D-212 and WATER LOCK D-242 are likewise suitable. These polymers have the chemical name starch-g-poly(2-propenamide-co-2-propenoic acid, mixed sodium and aluminum salt). The superabsorbent polymer commercially available under the trademark WATER LOCK G-400 is also suitable for use in the making of the hydrophilic foam composition of the present invention. This superabsorbent polymer may be chemically identified as a poly(2-propenamide-co-2-propenoic acid, sodium salt). Other super absorbent powders suitable for use in the present invention are sold by Grain Processing Corporation under the trademark WATER LOCK B, C, and H.

Another example of a suitable superabsorbent polymer is poly-2-propenoic acid, sodium salt, sold under the trademark absorbent polymers sold by Arakawa Chemical (USA) Inc. under the trademark ARASORB are also suitable. The preferred hydrophilic polymers are WATER LOCK A-100, A-200, A-222 and AQUA KEEP J-500. The hydrophilic polymers may be used alone, or in combination, to achieve the desired absorptivity characteristics in the foam composition.

The hydrophilic agent may comprise additives in addition to the superabsorbent polymers, provided, as discussed above, the additives do not reduce the fluid uptake of the hydrophilic agent to below about 50 ml water per gram of hydrophilic agent and the fluid uptake of the final foam composition is not less than about 3 times its weight. Examples of such additives include methylcellulose, guar gum, pectin, karaya gum, chitosan, agar, acacia powder, carrageenan, gelatin, and combinations thereof.

The amount of hydrophilic agent used and the type of agent, in terms of its fluid uptake, that may be satisfactorily used to make the foam composition is not critical, but is, instead, dependent on the intended application of the resulting foam composition. Stated another way, the greater the quantity of external liquid to be absorbed, e.g., the greater the amount of wound exudate, the greater the amount of hydrophilic agent that should be employed. In the alternative, the greater the amount of wound exudate to be absorbed, the greater the fluid uptake of the hydrophilic agent should be. For example, for an ulcerated wound where there is a high volume of wound exudate, a hydrophilic agent with high uptake is desirable. In addition, it may well be determined that the amount of hydrophilic agent may need to be increased. On the other hand, where the foam is to be applied to a small cut or light burn, it may be suitable to use less hydrophilic agent or to use a hydrophilic agent with a lower fluid uptake. Determination of the type and amount of hydrophilic agent used is well within the ability of one skilled in the art in light of the disclosure herein.

The amount of hydrophilic agent utilized should not be so great as to undesirably reduce the strength of the foam composition or result in a loss of polymer from the foam, although some loss of hydrophilic agent may be tolerated without adversely affecting the ability of the foam to absorb external liquids. The amount of hydrophilic agent employed in the reactant composition will also depend on the absorbency of the material used. As previously indicated, it is preferable that a sufficient amount of hydrophilic agent be employed so that the resulting foam composition is capable of absorbing at least about three times its weight in external liquid. Typically this can be achieved by including from about 5 wt. % to about 20 wt. % hydrophilic agent in the reactant composition.

The reactant composition of this invention may further include an adjuvant; preferably, a water-soluble adjuvant. The adjuvant is releasably carried by the resulting foam composition for subsequent release to a chosen situs of application. Release of the adjuvant occurs in the presence of an external liquid, such as wound exudate, which is preferentially absorbed by the foam composition. Absorption of the external liquid causes at least a portion of the adjuvant to be released.

It will be appreciated by those skilled in the art that not all of the liquid adjuvant is necessarily released (or need it be) in the presence of the external fluid. However, a sufficient amount of adjuvant must be released in order to achieve the desired result. To that end, it will be appreciated that the efficacy of the adjuvant is realized upon its release from the foam composition to the situs of application. In the case of a wound dressing, the situs is the wound, burn or the like, itself. Release of the adjuvant thus provides beneficial treatment to the wound.

Prior to curing, the adjuvant serves as a plasticizer for the reactant composition. It extends the curing time of the composition thereby allowing it to be more thoroughly mixed and formed. Once cured, the foam composition is softened by the adjuvant, allowing the foam to be more pliable and more easily applied to the skin surface or other surface of choice. Additionally, the adjuvant may be somewhat hygroscopic lending further to the hydrophilic nature of the foam composition.

Adjuvants suitable for use in the foam composition of the present invention are mono, di and polyhydric alcohols. Preferably the adjuvants are water soluble so that they may be readily released from the composition upon contact of the foam composition with an external liquid. For wound dressing applications, it is also desirable that the adjuvant be capable of contacting skin without adverse side effects. To that end, it is also preferable that the adjuvant comprise a chemical compound that will have the ability to open the skin pores to achieve a demulcent effect to relieve pain and/or irritation and to achieve an emollient effect to soften the skin and prevent maceration. It is also preferred that the adjuvant be compatible with therapeutic or other agents which may be carried by the adjuvant for subsequent delivery to the situs of application. Suitable adjuvants include water soluble alcohols, including monols, diols and polyhydric alcohols. Examples of monols include ethyl alcohol and isopropyl alcohol. Exemplary of suitable diols are propylene glycol, polyethylene glycol, and polypropylene glycol. Exemplary of suitable polyhydric alcohols are glycerin, 1,2,4-butanetriol, trimethylolpropane, pentaerythritol, and sorbitol. In general, the molecular weight of the alcohols should be less than about 1000. Mixtures of alcohols can likewise be used.

Glycerin is the preferred adjuvant because it has the attributes of a medicament, cosmetic, or therapeutic agent. When glycerin is used and the hydrophilic agent is starch-based, it is believed that glycerin coats the hydrophilic agent to form a starch glycerite. When fluid is absorbed by the foam, glycerin is released, thereby allowing the hydrophilic agent to swell as it absorbs fluid from the wound and causing the foam to conform to the wound contour.

Various additional medicaments, cosmetics, and therapeutic agents may, if desired, be carried with the adjuvant and released with it to the desired situs. This release thus allows the transmission of such therapeutic or other agents carried in the adjuvant to the area of application outside the foam composition, further assisting in the beneficial treatment of the wound.

Illustrative of therapeutic agents which may be incorporated into the foam composition are Collasol 2400, Crotein SPA, Cromoist HYA, Crotein CAA and hydrocortisone acetate. Illustrative of cosmetic agents which may be incorporated into the foam composition are European Collagen Complex, Capture Complex Liposomes, Sardo ® bath oil, a hand lotion sold under the trademark Jergens ®, Noxema ® skin cream, Oil of Olay ® BF, Keri ® lotion, Vaseline ® herbal and aloe lotion, Ben Gay ® ointment, and Retin-A ® cream.

The amount of adjuvant included in the reactant composition should preferably be sufficient to impart softness and pliability to the foam composition and be capable of delivering a therapeutic agent or the like, if included, to the environment of application. However, the volume of adjuvant should not be so great as to weaken or gel the composition. Generally, it has been found that the amount of adjuvant in the reactant composition should be from about 5 wt. % to about 30 wt. % of the reactant composition.

A wetting agent may be included in the reactant composition to provide more uniform wettability of the resulting foam. The wetting agent also aids in controlling the cell size of the foam and in the reticulation of the final foam. Wetting agents suitable for use include non-ionic surfactants. Examples of materials that may be used as the wetting agent, either alone or in admixture, include block copolymers of ethylene oxide and propylene oxide sold under the trademark PLURONIC by BASF Wyandotte Corporation, ethoxylated sorbitan fatty acid esters, glycerol esters, polyglycerol esters, and silicone fluids. PLURONIC F-68 and L-62 are preferred. As is known, PLURONIC F-68 aids in wound cleansing without causing tissue damage. The use of PLURONIC F-68 is especially preferred because of its cleansing action, particularly because a portion of the surfactant may be released when the foam composition is exposed to the exudate of the wound. Generally, the amount of wetting agent should be from about 1% to about 10% by weight of the reactant composition, preferably from about 5% to about 7% by weight.

The wetting agent should not react with the foam composition or any component of the foam formulation to create difficulties during foam formation or to adversely affect the desired characteristics of the foam composition in use or while being stored.

Water is a necessary component of the reactant composition as its presence results in the initiation of the foaming reaction. It should be appreciated that the source of the water required for the foaming reaction is not critical. The water so required may be provided as a separate component of the reactant composition, or, for example, it may be provided by one of the other components of the reactant composition. By way of illustration, and not in limitation, the required water may be provided with an aqueous-based cosmetic which may be incorporated into the foam composition.

The type of water used is likewise not critical. However, for medical applications, purified water such as deionized or distilled water may be used. Saline solutions may also be used satisfactorily.

It will be appreciated that the relative proportion of prepolymer, adjuvant and hydrophilic agent, if the latter two are included in the reactant composition, can be varied over wide ranges in order to prepare a hydrophilic foam composition having the desired release and exchange characteristics previously described, while likewise providing a foam composition that is aesthetically satisfactory, insofar as its oilyness, touch, appearance and general feel. In general, for use as a wound dressing, it is preferable that the foam composition be soft and generally smooth to the touch so that it does not irritate the skin. These characteristics may be achieved by properly balancing the relative proportion of adjuvant, prepolymer, hydrophilic agent, wetting agent, and water.

By way of illustration, it has been found that if excess glycerin is used in the reactant composition the resulting foam composition has an extended cure time and a decreased ability to tightly hold external liquid. Further, it may have an oily or spongy nonuniform surface. On the other hand, if insufficient glycerin is included in the reactant composition, the resulting foam composition has been found to be less uniform, has relatively poor flow and porosity characteristics, has relatively poor dimensional stability, and absorbs liquid at a slower rate.

Similarly, if the relative proportion of prepolymer to hydrophilic agent is too high or too low, the resulting product will not be satisfactory. The amount of hydrophilic agent must be sufficient to absorb the external liquid and to promote the release of the adjuvant. If the amount of hydrophilic agent is too low, there is insufficient absorption of external liquid. On the other hand, if the amount of hydrophilic agent is too high, then the viscosity of the reactant composition will be too high for appropriate mixing.

In general, in order for the foam composition to have the desired liquid release and exchange characteristics and to provide a foam composition that is soft to the touch and not oily, the weight ratio of prepolymer to hydrophilic agent will desirably be in the range of from about 20:1 to about 20:10 and the ratio of prepolymer to adjuvant will desirably be in the range of from about 20:2 to about 20:30.

It will likewise be appreciated that the wetting agent employed and the amount used may effect the characteristics of the resulting foam composition. It is generally desired that the wetting agent be used in an amount such that the foam is substantially uniform and readily wettable.

Throughout this disclosure, and for purposes of illustration only, the invention will be described in detail by referring to the production of a foam product which is manufactured using an isocyanate-capped prepolymer. However, it should be understood we do not intend to be limited to this single prepolymer or to the specific conditions and components contained in the illustrative example, and any prepolymers which function in the same manner as the illustrative isocyanate-capped prepolymer may be satisfactorily employed.

By way of illustrating the process and apparatus of the present invention, the preparation of a reaction product using the preferred component composition disclosed in U.S. Ser. No. 175,036 will be discussed. This composition comprises an isocyanate-capped prepolymer, a hydrophilic agent, water, a wetting agent, and an adjuvant.

Once the prepolymer is selected, the reaction product may be prepared by simply mixing the reactants until they are well blended. This method is preferred when only water and a prepolymer are used to produce the reaction product. However, when additional components are introduced, as in the illustrative example, it is preferable to separately prepare an aqueous phase or phases and an organic phase or phases, with the prepolymer being confined separately. The aqueous phase is prepared by dissolving the hydrophilic agent and wetting agent in water. Heat may be required in order to fully dissolve or disperse the wetting agent. An organic phase or phases may also be prepared if there is an organic component other than the hydrophilic agent. In the illustrative example, the adjuvant is the only other component other than the polymer itself which will comprise the organic phase and, as such, it may be simply contained within a reservoir tank until needed.

Although the aqueous phase may be prepared at ambient temperature, it is preferable to maintain the temperature of the aqueous phase at from about 60° F. to about 120° F., particularly when a wetting agent is used. The temperature at which the aqueous phase is most advantageously maintained is about 100° F. This temperature is preferred due to its advantageous effect upon the dispersion of the components in the aqueous phase as well as its effect on the rate of the water-prepolymer reaction.

After each of the aqueous and organic phases are separately prepared, they are combined with the prepolymer and allowed to react and form the reaction product. It should be appreciated that the various blends and phases may be prepared by either a batch process or a continuous process.

Turning to FIG. 1 which serves to illustrate the present method and apparatus of the present invention, the adjuvant (or organic phase), prepolymer, and aqueous phase are transferred via inlet tubes 1, 2, and 3 to a suitable reaction vessel 4 in which the phases and prepolymer are combined for reaction. The reaction vessel 4 merely serves to mix the reactants sufficiently such that they will react to form the reaction product. The vessel 4 is preferably equipped with speed-controllable mixing paddles to blend the phases and a temperature control means for controlling the temperature of the reactants.

The mixing speed of the vessel 4 and its temperature are preferably set to a predetermined level as a variance in either parameter will affect the properties of the resulting foam sheet. Generally, the predetermined levels are dependent on the flow rates of each component and more specifically on the combined flow rate. For example, if the mixer revolutions per minute (rpm) is too low, inadequate mixing of the reactants results. If the mixer rpm is too high, the heat build up due to the high setting increases the reaction rate of the reactants, thereby effecting the subsequent processing of the reaction product. By way of illustration, if the reaction proceeds too quickly, the reaction product may prematurely cure such that the thickness of the resulting product may not be able to be as accurately controlled by the subsequent compression step. This phenomenon will be explained in more detail hereinafter. Premature failure of parts and excessive use of energy may also occur when the mixing speed is not optimized.

The temperature of the mixer is generally kept lower than the temperature of the reactants because the reaction itself is exothermic. If the temperature is too high, the reaction will proceed at a much higher rate, thereby effecting subsequent processing of the foam, for the reasons stated previously, and also shortening the cure time. Excessive temperatures can also cause an imbalance in carbon dioxide generation and polymerization which may result in a nonuniform product.

The mixing vessel is thus desirably operated at a mixing speed in the range of from about 100 to about 10,000 rpm, and at a temperature within the range of from about 60° F. to about 120° F. Optimally, the aqueous and organic phases are mixed in vessel 4 at a mixing speed of approximately 2500 rpm and at a temperature of about 90° F.

After the mixing process is completed, the reaction product is discharged from vessel 4 through a nozzle 7 onto a continuously moving substrate 5. The method of and means for depositing the reaction product onto the substrate 5 is not critical to the process of the present invention so long as the reaction product develops a generally uniform thickness prior to being crushed between rollers 9 and 10.

The substrate may be driven by a conveyer belt 6 or, alternatively, the substrate may be drawn in a controlled tension environment such that it will move at the same speed as a conveyor belt would if said belt were used. The controlled tension environment is created by a winder which is located at the end of the production line. As presently contemplated, the turning of this winder will not only wind the finished product into a jellyroll configuration, but will also serve to pull the substrate through the process. Thus, the force exerted by this environment should be sufficient to unwind the substrate from its source and move it through the crushing rollers as well as any additional processing devices that might be present. If this environment is selected, the substrate may either contact or not contact a non-driven conveyor.

In keeping with the present invention, the substrate 5 moves forward relative to the nozzle 7, at the same velocity as the conveyer 6. The flow rate of the reaction product from the nozzle 7 and the velocity of the substrate 5 combined affect the thickness and width of the resulting foam sheet. The velocity of the substrate is directly proportional to the reaction time of the reaction product prior to compression by a first set of compression rollers and effects the nature of the reaction product. For example, the slower the velocity of the substrate, the greater the reaction time (the time between deposition and the initial compression) and the less the width of the final product.

More particularly, the present method and apparatus contemplate that the conveyer 6 be designed so as to allow the velocity of the substrate to vary from about 0.1 to about 11 feet per minute, with the rate at which the reaction product is deposited onto the substrate 5 through nozzle 7 being within the range from about 0.1 to about 2.0 pounds per minute. In the preferred embodiment of this invention where the reaction product leaves the reaction vessel at 90° F. after being mixed at 2500 rpm, the reaction product is deposited onto the substrate 5 at a rate of approximately 0.2 pounds per minute and the substrate 5 travels at a velocity of 5.0 feet per minute.

The composition of the substrate material 5 onto which the reaction product is deposited may vary considerably without materially effecting the present process. For example, the substrate may be a porous or non-porous paper or derivative thereof, a type of liner onto which the reaction product will be releasably adhered, a transfer adhesive, or a partially or completely adhesively coated material. However, the material selected must be able to withstand the subsequent processing to which it will be subjected. It is therefore advantageous for the substrate to comprise an adhesive-coated plastic, such as polyurethane or polyvinylidene chloride (saran). The saran should preferably be approximately 1.0 mil in thickness and be laminated to an approximately 5.5 mil coated paper for support. Adhesives that are suitable for use will depend upon the end use application of the device. For example, where the device will be used for wound dressings, suitable adhesives include medical grade acrylic adhesives.

The process, as contemplated, is advantageously carried out under a cover or hood. The cover serves to prevent unwanted particulate matter from becoming entrained within the reaction product during processing.

After the reaction product is deposited onto the substrate, but before the reaction product is subjected to its initial compression by rollers 9 and 10, a cover sheet 8 may be deposited onto the product to form a composite. The cover sheet 8, which has previously been release coated, is thus releasably adhered to the product. Advantageously, the cover sheet 8 is a release coated paper or plastic. It is preferred that a polystyrene sheet be used due to its flexibility, availability, and low cost. The polystyrene sheet preferably has one side release coated and is approximately 5.5 mils in thickness.

The cover sheet 8 may be supplied by any type of suitable device, but preferably the device will provide a continuous supply of cover sheet material. The cover material is positioned onto the surface of the reaction product by a roller. Advantageously the roller which positions the cover sheet may be the same roller that applies the initial compressive force to the reaction product.

Subsequent to, or simultaneously with, the application of the cover sheet 8, the composite is subjected to a compressive force which serves to control the thickness of the resulting foam sheet product. It should be appreciated that the timing of the compression is critical to the success of the novel process. Specifically, the first compression should not occur until the reaction product has creamed, i.e., until such time as the reaction product begins to foam and rise.

While it is contemplated that the composite may undergo only one compression, it is preferred that it undergo multiple compressions. The compressions are preferably accomplished on a continuous basis by passing the composite through a series of compression means, which in the preferred embodiment comprise a pair of rollers 9, 10 which define a gap 16 therebetween. The compression means compress the creamed foam so as to effect a reduction in foam thickness of from about 5 to about 95 percent of the foam thickness just prior to compression. Reductions of that magnitude may be effected for each of a plurality of compressions. It will be appreciated by those skilled in the art that the number of compressions, degree of compression, and the timing of the compressions is critical to the properties of the final product. These factors will affect the physical properties of the resulting product. More specifically, the density, thickness, width, and appearance of the product will be affected. In order to determine the number and degree of compressions for the particular reaction product and processing conditions employed, a measurement of the foam thickness of the reactant product that has been removed from the conveyor just after each sequential compression should be taken after the foam has been allowed to rise to its fullest extent. This measurement should be compared with a measurement taken of the thickness of the foam reaction product that has similarly been allowed to rise to its fullest extent without undergoing that compression. Such a comparison will allow an operator to determine both the number of compressions and the degree of compression needed to attain a foam having the desired final thickness.

When the compression means comprise at least one pair of spaced apart rollers, which define a gap therebetween through which the composite will pass, as in the illustrative embodiment, the gap between the rollers should be such that the foam will be compressed in the amount of from about 5 percent to about 95 percent, based on the thickness of the foam reaction product as determined by measurements taken of the foam at the times and under the conditions specified in the previous paragraph. For the calculation of the gap between the compression rollers and the placement of the compression rollers from the nozzle, several factors have to be considered. These include the cream and rise times of the reaction product, the percent rise of the reaction product per unit of time, the desired final product characteristics, substrate speed, and the like. These factors should be taken into account when changing conveyor speed, product width or thickness, product formulation, or the like. The rollers should preferably be adjustable to within 0.001 inch. Optimally, these adjustments are made with reference to manually adjustable micrometers which are located on the ends of said rollers. According to the illustrative example, three sets of rollers, 9 and 10, 11 and 12, and 13 and 14, are used.

In the illustrative embodiment of the invention, the initial compression preferably reduces the thickness of the reaction product by about 80 percent, and each subsequent compression reduces the thickness by about 40 percent. Compressing the composite in this manner results in a superior final foam product that will emerge having a specific, predetermined thickness. For example, when the velocity of the substrate 5 is 5.0 feet per minute, and the reaction product, which is produced from an isocyanate-capped polyether prepolymer, water, a hydrophilic agent, a wetting agent, and an adjuvant, is deposited at a rate of 0.2 pounds per minute, it is preferred that the initial compression, which compresses the foam about 80 percent, occur after the reaction product begins to cream, but no later than 2 seconds after the reaction product leaves the nozzle 7. The second and third compressions, each of which compresses the foam about 40 percent, should also occur within 55 and 70 seconds, respectively, after the material has left the nozzle 7.

After the final compression, and after the product no longer adheres to the cover sheet, it is preferred that the cover sheet 8 be removed and the product finally cured. Alternatively, the cover sheet 8 may remain in contact with the reaction product until the reaction product is finally cured, or beyond this time.

An important aspect of the present invention is the production of a foam product without the application of heat to effect the curing process. More specifically, from the time the reaction product leaves the nozzle 7, until the time it is finally cured, the reaction product undergoes processing at ambient temperature. Processing foams of the type contemplated by the present invention at ambient temperature is advantageous in that less energy is consumed and less volatilization of components occurs.

Upon completion of the curing stage of the process, the resulting foam sheet product is at the desired predetermined thickness. No slicing of the foam to achieve the desired thickness is necessary. This results in energy and labor savings to the foam sheet producer, making the present novel method and apparatus highly desirable when compared with other available methods.

If desired, the foam sheet may subsequently be subjected to drying means wherein the foam sheet is dried to a predetermined moisture level. Preferably the moisture level in the final foam product is 10 percent by weight. The moisture level of the foam is important in that the softness, texture, and wettability of the resulting product are affected by variations in the moisture level. Further, the less moisture in the foam, the more liquids it will absorb and the less problems there will be with warped packaging. Advantageously, drying is carried out using hot air impingement, with the air that is used for the dryer being first drawn through a particulate filter. It is preferable that drying be conducted while the foam is still on the conveyor, but after the cover sheet is removed to enhance drying.

Returning to the illustrative example, the drying temperature should range from about 100° F. to about 175° F. because the components of the product may be volatile or may undergo changes at temperatures higher than 175° F., e.g., the product discolors. Preferably, the temperature is maintained at 140° F.

The process further contemplates a dryer 15 which is between 2 and 20 feet in length. The dryer is capable of producing a volume of drying air varying from about 100 to 1000 cubic feet per minute (CFM). In the preferred embodiment, the product is dried in a 20 foot dryer at a temperature of 140° F. with air being supplied at a rate of 500 CFM, such that the resulting product will have a final moisture content of approximately 10 percent by weight.

The resulting foam sheet product may then be rolled, sterilized, and packaged in an air-impervious container. Alternatively, the sheet may be cut into predetermined lengths or shapes for use in bandages or other wound dressings of various sizes.

Thus, as has been shown, the present invention provides a process that is more expeditious than those processes employed in the past for manufacturing sheets of foaming polymers. The process of the present invention is not only a more energy efficient process, but also one that allows for a higher degree of quality and uniformity of product than was previously thought possible.

We claim as our invention:

1. A continuous process for the preparation of a polymer-based porous cellular foam sheet of a predetermined thickness wherein the foam is produced from a reaction product capable of curing at ambient temperature formed by the reaction of a reactant composition comprising a prepolymer and water, said process comprising:
   (a) providing a continuously moving substrate for supporting the foam sheet being formed;
   (b) depositing said reaction product onto said substrate at a rate and in an amount such that the thickness of the sheet formed by the reaction product, if allowed to rise to its fullest extent without undergoing compression, would be greater than said predetermined thickness;
   (c) allowing said reaction product to begin rising to form a rising foam sheet;
   (d) passing said rising foam sheet into and through a compression zone;
   (e) compressing said rising foam sheet to a predetermined degree while maintaining the thus-compressed thickness of the rising foam sheet constant as it passes through said compression zone;
   (f) removing said rising foam sheet from said compression zone;
   (g) allowing the rising foam sheet exiting from said compression zone to rise to provide a porous cellular foam sheet of said predetermined thickness; and
   (h) finally curing said foam sheet.

2. The process of claim 1, wherein said prepolymer is a polyurethane prepolymer.

3. The process of claim 2, wherein said polyurethane prepolymer is an isocyanate-capped polyether prepolymer.

4. The process of claim 1, wherein said rising foam sheet is passed through a plurality of said compression zones.

5. The process of claim 1, wherein said substrate is releasably adhered to said reaction product.

6. The process of claim 1, wherein said substrate is adhered to said reaction product.

7. The process of claim 1, wherein said substrate is selected from the group consisting of polyvinylidene chloride and polyurethane.

8. The process of claim 1, further comprising covering said reaction product with a cover sheet after said deposition step to form a composite.

9. The process of claim 8, wherein said cover sheet is releasably adhered to said reaction product.

10. The process of claim 8, wherein said cover sheet is comprised of paper.

11. The process of claim 8, wherein said cover sheet is comprised of plastic.

12. The process of claim 11, wherein said cover sheet is comprised of polystyrene.

13. The process of claim 8, further comprising removing said cover sheet after said reaction product is finally cured.

14. The process of claim 1, further comprising drying said reaction product after said product has finally cured.

15. The process of claim 14, wherein said drying is accomplished by dry air impingement.

16. The process of claim 14, wherein said drying is conducted until said reaction product has a moisture content of about 10 percent by weight.

17. The process of claim 1, wherein said process is carried out in a particulate-free environment.

18. The process of claim 1, wherein the predetermined degree of compression is in the range of from about 5 percent to about 95 percent of the thickness of said foam sheet just prior to said compression.

19. The process of claim 1, wherein said rising foam sheet is passed through a plurality of compression zones and the degree of each compression is in the range of from about 5 percent to about 95 percent of the thickness of said foam sheet just prior to said compression.

20. The process of claim 1, said reactant composition further comprising a hydrophilic agent capable of absorbing water.

21. The process of claim 20, said reactant composition further comprising an adjuvant comprising an alcohol.

22. The process of claim 21, wherein said alcohol is selected from the group consisting of water soluble monols, diols, and polyhydric alcohols.

23. The process of claim 22, further comprising a wetting agent.

24. The process of claim 23, wherein said prepolymer is selected from the group consisting of isocyanate-capped polyether polyols having an isocyanate equivalent weight of from about 0.5 meq/g to about 2.5 meq/g and mixtures thereof.

25. The process of claim 23, wherein said prepolymer is present in an amount of from about 20 wt. % to about 50 wt. % of the total reactant composition.

26. The process of claim 23, wherein said prepolymer is present in an amount of from about 45 wt. % to about 50 wt. % of the total reactant composition.

27. The process of claim 23, wherein said hydrophilic agent is an absorptive polymer capable of absorbing water and having a fluid uptake of at least about 50 ml of water per gram of said polymer.

28. The process of claim 23, wherein said hydrophilic agent is an absorptive polymer having a fluid uptake of at least about 100 ml of water per gram of said polymer.

29. The process of claim 23, wherein said hydrophilic agent is an absorptive polymer having a fluid uptake of at least about 150 ml of water per gram of said polymer.

30. The process of claim 23, wherein said hydrophilic agent is a member selected from the group consisting of starch grafted copolymers of acrylate salts, starch grafted copolymers of acrylamide salts, polyacrylate salts, and mixtures thereof.

31. The process of claim 23, wherein said hydrophilic agent is present in an amount sufficient to provide a foam composition capable of absorbing at least about 3 times its weight of liquid.

32. The process of claim 30, wherein said hydrophilic agent is present in an amount sufficient to provide a foam composition capable of absorbing at least about 3 times its weight of liquid.

33. The process of claim 31, wherein said foam composition is capable of tightly carrying at least about 3 times its weight of liquid.

34. The process of claim 32, wherein said foam composition is capable of tightly carrying at least about 3 times its weight of liquid.

35. The process of claim 23, wherein said alcohol is a monol.

36. The process of claim 23, wherein said alcohol is a diol.

37. The process of claim 23, wherein said alcohol is a polyhydric alcohol.

38. The process of claim 37, wherein said polyhydric alcohol has a molecular weight of less than about 1000.

39. The process of claim 23, wherein said alcohol is a member selected from the group consisting of isopropyl alcohol, ethanol, propylene glycol, polyethylene glycol, polypropylene glycol, glycerine, 1,2,4-butanetriol, trimethylolpropane, sorbitol, pentaerythritol, and mixtures thereof.

40. The process of claim 32, wherein said alcohol is glycerin.

41. The process of claim 23, wherein said alcohol is present in an amount of from about 5 wt. % to about 30 wt. % of the reactant composition.

42. The process of claim 23, wherein said wetting agent is a non-ionic surfactant selected from the group consisting of block copolymers of ethylene oxide and propylene oxide, ethoxylated sorbitan fatty acid esters, glycerol esters, polyglycerol esters, silicone fluids and mixtures thereof.

43. The process of claim 42, wherein said wetting agent is present in an amount of from about 1 wt. % to about 10 wt. % of said reactant composition.

44. The process of claim 23, wherein said prepolymer, said hydrophilic agent and said adjuvant are present in the reactant composition such that the ratio of prepolymer to hydrophilic agent is in the range of from about 20:1 to about 20:10 and the ratio of prepolymer to adjuvant is in the range of from about 20:2 to about 20:30.

45. The process of claim 44, wherein said prepolymer is a member selected from the group consisting of isocyanate-capped polyether polyols having an isocyanate equivalent weight of from about 0.5 meq/g to about 2.5 meq/g, said hydrophilic agent is a member selected from the group consisting of starch grafted copolymers of acrylate salts, starch grafted copolymers of acrylamide salts, polyacrylate salts and mixtures thereof; said adjuvant is a member selected from the group consisting of ethanol, isopropyl alcohol, propylene glycol polyethylene glycol, polypropylene glycol, glycerine, 1,2,4-butanetriol, trimethylolpropane, sorbitol, pentaerythritol, and mixtures thereof; said reactant composition includes a wetting agent and said wetting agent is a member selected from the group consisting of block copolymers of ethylene oxide and propylene oxide, ethoxylated sorbitan fatty acid esters, glycerol esters, polyglycerol esters, silicone fluids and mixtures thereof, and said water is a member selected from the group consisting of deionized water, distilled water and normal saline.

46. The process of claim 45, wherein said prepolymer is an isocyanate-capped polyether prepolymer having an isocyanate equivalent weight of about 1.6 meq/g and an equivalent weight per isocyanate group of about 625; said hydrophilic agent is starch-g-poly(2-propenamide-co-2-propenoic acid, mixed sodium and aluminum salt); said adjuvant comprises glycerine, and said wetting agent is a member selected from the group consisting of block copolymers of ethylene oxide and propylene oxide.

47. A continuous process for the preparation of a polymer-based porous cellular foam sheet of a predetermined thickness wherein the foam is produced from a reaction product capable of curing at ambient temperature formed by the reaction of a reactant composition comprising an isocyanate-capped polyether prepolymer and water, said process comprising:

(a) providing a continuously moving substrate at a rate of about 0.1 to about 11 feet per minute;

(b) depositing said reaction product onto said substrate at a rate of from about 0.1 to about 2.0 pounds per minute and such that the thickness of the sheet formed by the reaction product, if allowed to rise to its fullest extent without undergoing compression, would be greater than said predetermined thickness;

(c) allowing said reaction product to begin rising to form a rising foam sheet;

(d) passing said rising foam sheet into and through a compression zone;

(e) compressing said rising foam sheet to compress said rising foam sheet to a predetermined degree while maintaining the thus-compressed thickness of the rising foam sheet constant;

(f) removing said rising foam sheet from said compression zone;

(g) allowing the rising foam sheet exiting from said compression zone to rise to provide a porous cellular foam sheet of said predetermined thickness; and (h) finally curing the foam sheet.

48. The process of claim 47, wherein said continuously moving substrate is provided at a rate of about 5 feet per minute and said reaction product is deposited onto said substrate at a rate of about 0.2 pounds per minute.

49. The process of claim 48, wherein the temperature of said reaction product upon deposition ranges from about 60° F. to about 120° F.

50. The process of claim 49, wherein the temperature of said reaction product upon deposition is about 90° F.

51. The process of claim 45, wherein the predetermined degree of compression is in the range of from about 5 percent to about 95 percent of the thickness of said foam sheet just prior to said compression.

52. The process of claim 45, wherein said rising foam sheet is passed through a plurality of compression zones and the degree of each compression is in the range of from about 5 percent to about 95 percent of the thickness of said foam sheet just prior to said compression.

53. The process of claim 52, wherein said rising foam sheet is passed through three compression zones with the degree of said first of three compressions being about 80 percent of the thickness of said foam sheet just prior to the first compression, the degree of said second compression is about 40 percent of the thickness of said foam sheet prior to the second compression, and the degree of said third compression is about 40 percent of the thickness of said foam sheet prior to the third compression.

54. The process of claim 47, wherein said rising foam sheet is passed through three compression zones.

55. The process of claim 47, further comprising covering said reaction product with a cover sheet after said deposition step to form a composite.

56. The process of claim 55, wherein providing said substrate is accomplished by means comprising a continuously moving conveyor belt.

57. The process of claim 55, wherein providing said substrate is accomplished by means comprising a winding device.

58. The process of claim 55, further comprising removing said cover sheet after said reaction product is finally compressed and said product no longer adheres to said cover sheet.

59. The process of claim 47, further comprising drying said product after said product is finally cured at a temperature ranging from about 100° F. to about 175° F.

60. The process of claim 59, wherein said drying is conducted at a temperature of about 140° F.

61. The process of claim 59, wherein said drying step is conducted in a particulate-free environment.

* * * * *